US009757088B2

(12) United States Patent
Roberts et al.

(10) Patent No.: US 9,757,088 B2
(45) Date of Patent: Sep. 12, 2017

(54) DETECTOR APPARATUS FOR CONE BEAM COMPUTED TOMOGRAPHY

(71) Applicant: Toshiba Medical Systems Corporation, Otawara-shi (JP)

(72) Inventors: Barry Roberts, Gurnee, IL (US); Zhengyan Wang, Antioch, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 264 days.

(21) Appl. No.: 14/540,973

(22) Filed: Nov. 13, 2014

(65) Prior Publication Data

US 2016/0135778 A1    May 19, 2016

(51) Int. Cl.
*A61B 6/03*    (2006.01)
*A61B 6/00*    (2006.01)

(52) U.S. Cl.
CPC ............. *A61B 6/547* (2013.01); *A61B 6/032* (2013.01); *A61B 6/035* (2013.01); *A61B 6/42* (2013.01); *A61B 6/4208* (2013.01); *A61B 6/4233* (2013.01); *A61B 6/4241* (2013.01); *A61B 6/4266* (2013.01)

(58) Field of Classification Search
CPC .......... A61B 6/032; A61B 6/035; A61B 6/42; A61B 6/4208; A61B 6/4233; A61B 6/547
USPC ....................................... 378/19; 250/370.09
See application file for complete search history.

(56) References Cited

U.S. PATENT DOCUMENTS

| | | | | |
|---|---|---|---|---|
| 5,982,845 A * | 11/1999 | Sidoti | ................... | G06T 11/006 378/4 |
| 6,078,639 A * | 6/2000 | Heuscher | .............. | G06T 11/006 378/15 |
| 6,097,784 A * | 8/2000 | Tuy | ........................ | G06T 11/005 378/15 |
| 6,104,775 A * | 8/2000 | Tuy | ........................ | G06T 11/005 378/15 |
| 6,154,516 A * | 11/2000 | Heuscher | ............... | A61B 6/032 378/15 |
| 6,163,617 A * | 12/2000 | Heuscher | .............. | G06T 11/006 382/132 |
| 6,185,271 B1 * | 2/2001 | Kinsinger | .............. | A61B 6/032 378/19 |
| 8,798,350 B2 * | 8/2014 | Zou | ........................ | G06T 11/006 378/21 |
| 9,020,092 B2 * | 4/2015 | Wang | ..................... | A61B 6/583 378/5 |
| 9,089,266 B2 * | 7/2015 | Zou | ........................ | A61B 6/032 |
| 9,119,589 B2 * | 9/2015 | Zou | ........................ | A61B 6/032 |
| 9,128,194 B2 * | 9/2015 | Zou | ........................ | G01T 1/171 |
| 9,155,515 B2 * | 10/2015 | Petschke | ............... | A61B 6/032 |
| 9,198,632 B2 * | 12/2015 | Zhang | .................. | A61B 6/5282 |
| 9,219,178 B2 * | 12/2015 | Zhang | ............... | H01L 31/02327 |

(Continued)

*Primary Examiner* — Allen C. Ho
(74) *Attorney, Agent, or Firm* — Oblon, McClelland, Maier & Neustadt, L.L.P.

(57) ABSTRACT

A computed tomography (CT) imaging apparatus includes a radiation source to emit X-rays while rotating in a predetermined trajectory; a plurality of detectors arranged in a circular ring and configured to detect the emitted X-rays; and processing circuitry to cause the radiation source to scan an object, and cause a subset of the detectors nearest to the radiation source to move in a direction intersecting with a plane of the predetermined trajectory of the radiation source in accordance with a determined location of the radiation source.

16 Claims, 8 Drawing Sheets

(56) References Cited

U.S. PATENT DOCUMENTS

| | | | | |
|---|---|---|---|---|
| 9,226,723 B2* | 1/2016 | Shi | ............... | A61B 6/5205 |
| 9,256,938 B2* | 2/2016 | Petschke | ............... | G06T 7/0012 |
| 9,274,066 B2* | 3/2016 | Ji | ............... | G01N 23/046 |
| 9,285,326 B2* | 3/2016 | Gagnon | ............... | A61B 6/032 |
| 9,292,946 B2* | 3/2016 | Zou | ............... | G06T 11/006 |
| 9,330,443 B1* | 5/2016 | Zou | ............... | G06T 5/002 |
| 9,345,445 B2* | 5/2016 | Petschke | ............... | A61B 6/584 |
| 9,402,591 B2* | 8/2016 | Zou | ............... | A61B 6/032 |
| 9,449,385 B2* | 9/2016 | Petschke | ............... | G06T 7/0012 |
| 9,462,983 B2* | 10/2016 | Zhang | ............... | A61B 6/4241 |
| 9,476,993 B2* | 10/2016 | Wang | ............... | G01T 1/17 |
| 9,482,630 B2* | 11/2016 | Wang | ............... | G01N 23/046 |
| 9,538,975 B2* | 1/2017 | Silver | ............... | A61B 6/5282 |
| 9,545,236 B2* | 1/2017 | Zhang | ............... | A61B 6/482 |
| 9,554,760 B2* | 1/2017 | Rodrigues | ............... | A61B 6/482 |
| 9,618,633 B2* | 4/2017 | Rodrigues | ............... | G01T 1/241 |

* cited by examiner

DETECTOR APPARATUS FOR CONE BEAM COMPUTED TOMOGRAPHY

FIELD

The exemplary embodiments described herein relate to computed tomography (CT) systems.

BACKGROUND

The X-ray beam in most computer tomography (CT) scanners is generally polychromatic. However, third-generation CT scanners generate images based upon data according to the energy integration nature of the detectors. These conventional detectors are called energy-integrating detectors and acquire energy integrated X-ray data. On the other hand, photon-counting detectors are configured to acquire the spectral nature of the X-ray source, rather than the energy integrated nature. To obtain the spectral nature of the transmitted X-ray data, the photon-counting detectors split the X-ray beam into its component energies or spectrum bins, and count a number of photons in each of the bins. The use of the spectral nature of the X-ray source in CT is often referred to as spectral CT. Since spectral CT involves the detection of the transmitted X-ray at two or more energy levels, spectral CT generally includes dual-energy CT by definition.

Spectral CT is advantageous over conventional CT as it offers the additional clinical information inherent in the full spectrum of an X-ray beam. For example, spectral CT improves discriminating tissues and differentiating between materials such as tissues containing calcium and iodine, and enhances the detection of smaller vessels. Among other advantages, spectral CT is also expected to reduce beam-hardening artifacts and to increase accuracy in CT numbers independent of individual scanners.

Conventional spectral CT approaches include the use of the integrating detectors in implementing spectral CT. One attempt included dual sources and dual integrating detector units that are placed on the gantry at a predetermined angle with respect to each other for acquiring data as the gantry rotates around a patient. Another attempt includes a single source that performs kV-switching and a single integrating detector unit that are placed on the gantry for acquiring data as the gantry rotates around a patient. Yet another attempt includes a single source and dual integrating detector units that are layered on the gantry for acquiring the data as the gantry rotates around a patient. All of these attempts at spectral CT are not successful in substantially solving issues such as beam hardening, temporal resolution, noise, poor detector response, poor energy separation, etc. for reconstructing clinically viable images.

Conventional spectral CT approaches also include the replacement of the conventional integrating detectors by photon-counting detectors in implementing spectral CT. In general, photon-counting detectors are costly and have performance constraints under high flux. Although at least one experimental spectral CT system has been reported, the costs of high-rate photon-counting detectors are prohibitive for a full-scale implementation. Despite some advancement in photon-counting detector technology, currently available photon-counting detectors still require solutions to implementation issues, such as polarization due to space charge build-up, pile-up effects, scatter effects, spatial resolution, temporal resolution, and dose efficiency.

BRIEF DESCRIPTION OF THE DRAWINGS

A more complete appreciation of the teachings of this disclosure and many of the attendant advantages thereof will be readily obtained as the same becomes better understood by reference to the following detailed description when considered in connection with the accompanying drawings, wherein.

DETAILED DESCRIPTION

In a hybrid PCCT design, a ring of sparsely distributed photon-counting detectors are used to acquire spectral information in a fourth-generation CT geometry, while energy-integrating detectors acquire data using a third-generation geometry. The fourth-generation design can overcome challenges facing photon-counting detector technology, while the third-generation data can be used to maintain the spatial resolution and noise characteristics of the reconstruction.

In one embodiment, there is provided a computed tomography (CT) imaging apparatus, comprising: (1) a radiation source configured to emit X-rays while rotating in a predetermined trajectory; (2) a plurality of detectors arranged in a circular ring and configured to detect the emitted X-rays; and (3) processing circuitry configured to cause the radiation source to scan an object, and cause a subset of the detectors nearest to the radiation source to move in a direction intersecting with a plane of the predetermined trajectory of the radiation source in accordance with a determined location of the radiation source.

In another embodiment, there is provided a computed tomography (CT) imaging method for a CT apparatus that includes a plurality of detectors arranged in a circular ring and configured to detect X-rays emitted from a radiation source that rotates in a predetermined trajectory, the method comprising: (1) causing the radiation source to scan an object, and (2) causing a subset of the detectors nearest to the radiation source to move in a direction intersecting with a plane of the predetermined trajectory of the radiation source in accordance with a determined location of the radiation source.

In another embodiment, there is provided a non-transitory computer-readable medium storing executable instructions, which when executed by a processor of a CT apparatus that includes a plurality of detectors arranged in a circular ring and configured to detect X-rays emitted from a radiation source that rotates in a predetermined trajectory, cause the computer processor to execute a method comprising: (1) causing the radiation source to scan an object, and (2) causing a subset of the detectors nearest to the radiation source to move in a direction intersecting with a plane of the predetermined trajectory of the radiation source in accordance with a determined location of the radiation source.

Figure 1:
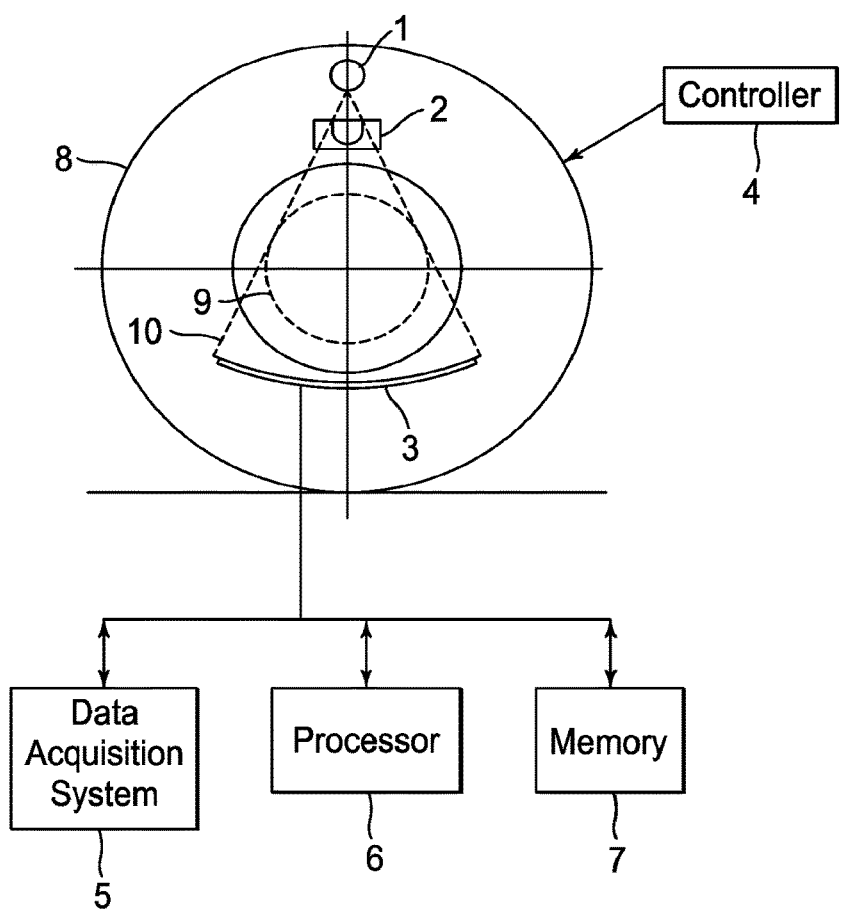
FIGS. 1 and 2 illustrate exemplary CT scanner systems.

FIG. 1 illustrates a simplified schematic structure of a CT apparatus that can include a detector 3 to detect photons. The detector 3 can include a plurality of detector elements.

Aspects of this disclosure are not restricted to a CT apparatus as the medical imaging system. In particular, the structures and procedures described herein can be applied to other medical imaging systems, and the descriptions provided herein specifically relating to a CT apparatus and the detection of photons should be considered as exemplary. A detector array, a photon detector and/or a photon detector array may be referred to herein merely as a detector.

Figure 2:
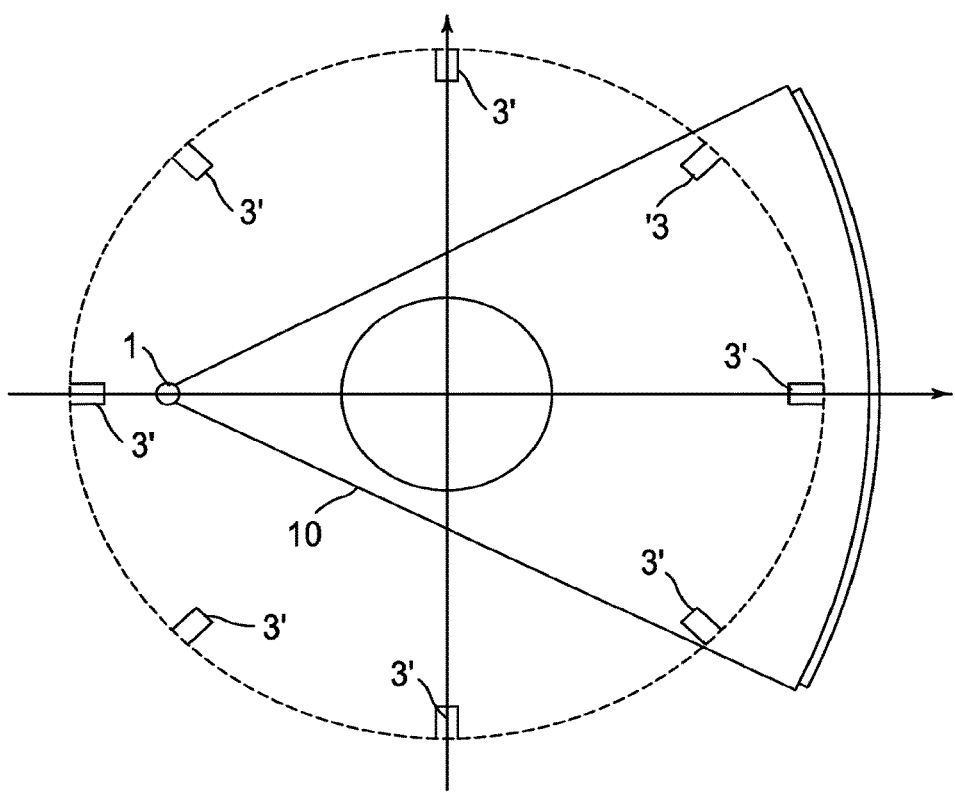

The CT apparatus illustrated in FIG. 1 includes an X-ray tube 1, filters and collimators 2, and a detector 3. The CT apparatus can also include sparse, fixed energy-discriminating (e.g., photon-counting) detectors 3', which can be arranged at a different radius from that of the third-generation detector, as shown in FIG. 2. The CT apparatus also includes additional mechanical and electrical components such as a gantry motor and a controller 4 to control the rotation of the gantry, control the X-ray tube 1, and control a patient bed. The CT apparatus also includes a data acquisition system 5 and a processor 6. The processor 6 is configured to generate CT images based on the projection (view) data acquired by the data acquisition system 5. For example, the processor 6 includes a reconstruction processor to reconstruct spectral CT images. The processor 6 is programmed to perform methods and execute algorithms in accordance with the processes, algorithms, equations and relationships described herein. The processor 6 and data acquisition system 5 can make use of a memory 7, which is configured to store, e.g., data obtained from the detector 3, detector pile-up models, and reconstructed images.

The X-ray tube 1, filters and collimators 2, detector 3, and controller 4 can be provided in a frame 8 that includes a bore. The frame 8 has a general cylindrical or donut shape. In the view shown in FIG. 1, a longitudinal axis of the bore of the frame 8 is in the center of the bore and extends into and out of the page. An interior of the bore, identified as area 9, is a target area for imaging. An object to be scanned, such as a patient, is placed in the target area with, e.g., a patient table. The object can then be irradiated by the X-ray tube 1 with a fan or cone of radiation 10, which generally, substantially or effectively cross-sects the object with respect to the longitudinal axis. The processor 6 is programmed to determine photon counts of captured incident X-ray photons. The data acquisition system 5, the processor 6, and the memory 7 can be implemented as a single machine or computer, or as separate machines or computers that are coupled together or distributed via a network or other data communication system. The controller 4 can also be coupled via the network or other data communication system, and can be implemented by a separate machine or computer, or as part of another machine or computer of the system.

In FIG. 1, the detector 3 is a rotational detector array that rotates with the X-ray tube 1 with respect to the longitudinal axis. A stationary detector array can also be included, thus providing a rotating detector array and a stationary array together in the frame 8. Other detector configurations can be implemented.

Figure 3:
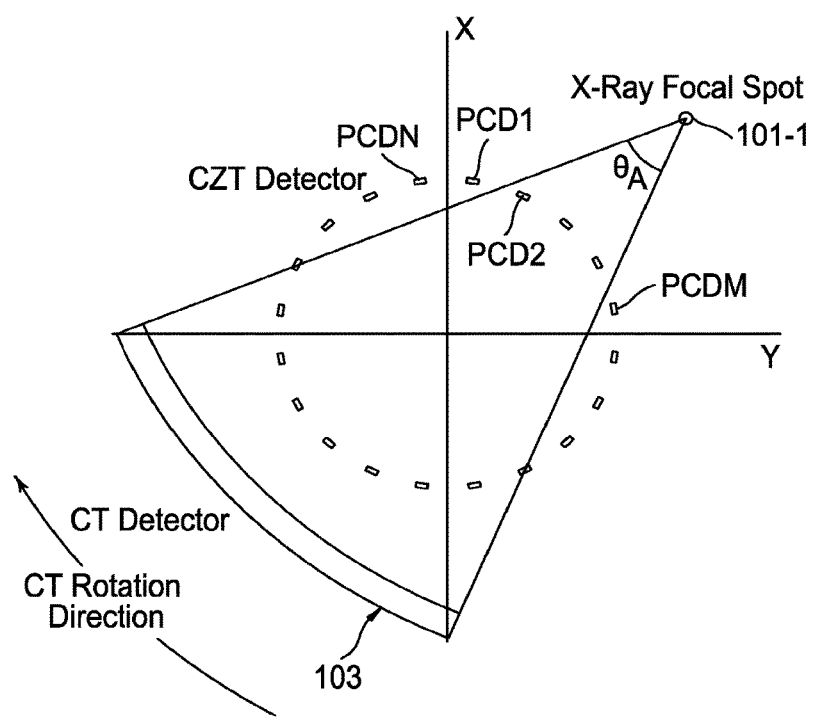
FIG. 3 shows an exemplary implementation of a computed tomography system with an stationary inner photon-counting detector ring.

Now referring to FIG. 3, a drawing illustrates an embodiment that includes photon-counting detectors (PCD) in a pre-determined fourth-generation geometry in combination with an X-ray source 101-1 with a corresponding detector 103 in a predetermined third-generation geometry. In addition to the sparse photon-counting detectors PCD1 through PCDN in the fourth-generation geometry, the exemplary embodiment of FIG. 3 further includes a detector 103 in a pre-determined third-generation geometry for detecting transmitted X-rays from the X-ray source 101-1 in the CT scanner system. The X-ray source 101-1 rotates outside the sparsely placed photon-counting detectors PCD1 through PCDN.

As shown in FIG. 3, since the X-ray source 101-1 travels outside the photon-counting detectors PCD1 through PCDN, the X-rays are projected through openings or gaps between the sparsely placed photon-counting detectors PCD1 through PCDN towards the object. Some portion of the emitted X-rays is blocked by some of the sparsely placed photon-counting detectors PCD1 through PCDN, depending upon the position of the X-ray source 101-1. In other words, a certain portion of the emitted X-rays project onto the back surface of some of the sparsely placed photon-counting detectors PCD1 through PCDN at any given time, as the X-ray source 101-1 is rotated around the predetermined trajectory. The remaining X-rays travel through the gap and reach some of the photon-counting detectors PCD1 through PCDN whose detecting surface is facing the X-ray source 101-1. Further, the remaining X-rays also reach the detector 103, whose detecting surface is substantially within the predetermined source fan beam angle $\theta_A$. Since the stationary photon-counting detectors PCD1 through PCDN on the side next to X-ray focal spot are blocking the X-rays that should pass though the body, a spectral CT system is needed to reduce the blockage.

Conventional attempts to improve the use of the photon-counting detectors include rotating a detector ring about a rotational direction to reduce the blockage of an X-ray source by parts of the detectors. In that system, all of the detectors are located along a predetermined circular component and form a detector ring. The detector ring performs a nutating motion in the rotational direction so that the detectors on the side closer to X-ray source, whose back surface is facing the X-ray source, do not block the detection of the X-ray by the detectors whose detecting surfaces is facing the X-ray source. However, the rotation of the detector ring involves all of the detectors attached to the predetermined circular components, while only a fraction of the detectors that block the X-ray detection need to be moved.

Figure 4:
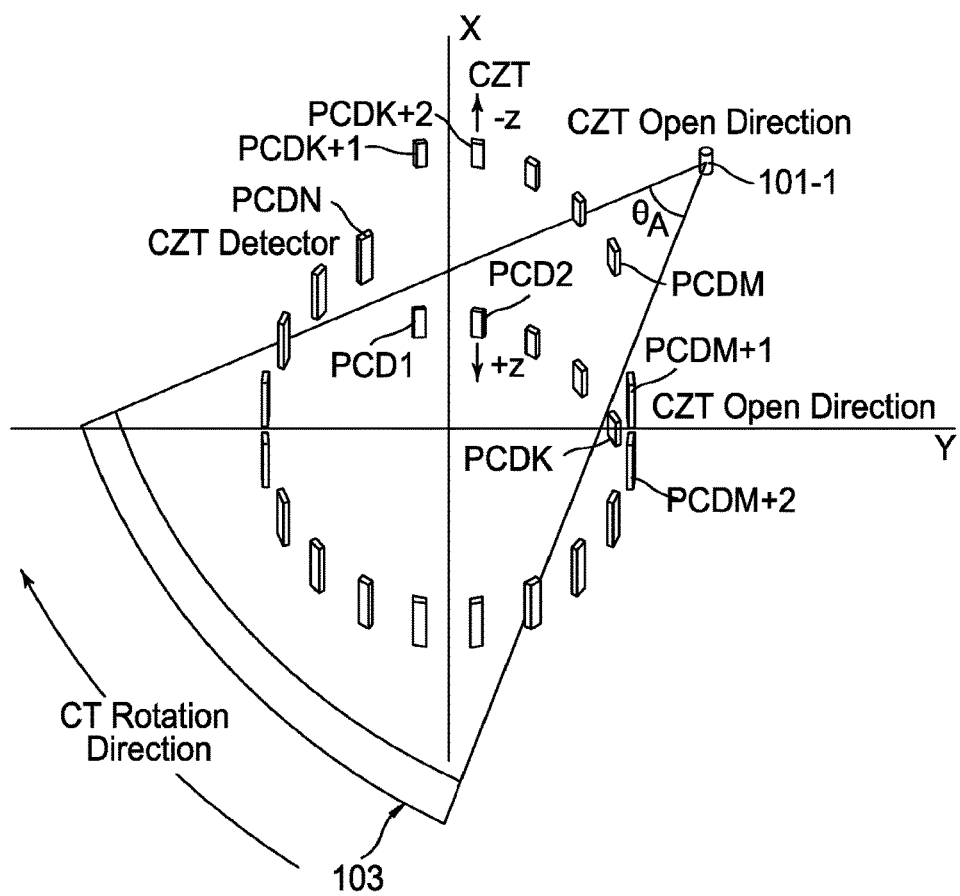
FIG. 4 shows an exemplary implementation of a computed tomography system with movable inner photon-counting detectors.

FIG. 4 illustrates an embodiment that includes photon-counting detectors in a predetermined fourth-generation geometry in combination with an X-ray source 101-1 with a corresponding detector 103 in a predetermined third-generation geometry. Both the X-ray source 101-1 and the detector 103 rotate around the object. The PCDs are sparsely placed along a first circular path around the object while the X-ray source 101-1 rotates along a second circular path around the object. The first circular path is smaller and inside the second circular path around the object. The X-ray source 101-1 projects X-rays with a predetermined source fan beam angle $\theta_A$ toward the object, while X-ray source 101-1 rotates around the object outside the sparsely placed photon-counting detectors PCD1 through PCDN. The detector 103 travels along a third circular path. A rotator portion mounts the detector 103 at a diametrically opposed position from the X-ray source 101-1 across the object and rotates outside the second circular path on which the photon-counting detectors PCD1 through PCDN are fixed placed in a predetermined, sparse manner.

In the present embodiments, a subset of detectors includes a first subset at an upper side of a plane and a second subset at a lower side of the plane, and processing circuitry that is configured to cause the first and second subsets to move in opposite directions. The subsets of detectors move in directions intersecting with a plane of the predetermined trajectory of the X-ray source 101-1 in accordance with a determined location of the X-ray source 101-1.

As shown in FIG. 4, the PCDs (PCD1 through PCDK) that are located on the closer side towards the X-ray source 101-1 are moved out from the trajectory plane (X-Y plane) of the radiation beam of the X-rays, and are split as two subsets of open-direction PCDs, wherein a first subset of open direction PCDs includes PCD1 to PCDK, and a second subset of open-direction PCDs includes PCDK+1 to PCDM. The first subset of PCDs is moved to a +z axis direction that is perpendicular to the trajectory plane of the radiation beam, and the second group of PCDs is moved oppositely in comparison with the first group of PCDs to a −z axis direction. Therefore, only the bottom detectors (PCDM+1 through PCDN) remain stationary and collect X-rays.

As the X-ray source 101-1 and the detector 103 rotate around the object, the photon-counting detectors (PCDs) and the detector 103 respectively detect the transmitted X-rays during the data acquisition. X-rays are projected through openings between the first subset and the second subset of open PCDs towards the object. Since the first subset of the PCDs (PCD1 through PCDK) is at a upper side of the trajectory plane of the X-ray source 101-1, and the second subset of the PCDs (PCDK+1 through PCDM) is at a lower side of the trajectory plane of the X-ray source 101-1, the emitted X-rays are no longer blocked by detectors PCD1 through PCDM of the sparsely placed photon-counting detectors PCD1 through PCDN. The first subset of the PCDs and the second subset of PCDs can be combined into a single subset of PCDs (PCD1 through PCDM). This single subset can be moved in either the +z axis direction or the −z axis direction so that the emitted X-rays are no longer blocked by detectors PCD1 through PCDM of the sparsely placed photon-counting detectors PCD1 through PCDN.

The X-rays travel through the opening and reach detectors PCDM+1 through PCDN of the photon-counting detectors PCD1 through PCDN, whose detecting surface is facing the X-ray source 101-1 and reach the detector 103, whose detecting surface is substantially within the predetermined source fan beam angle $\theta_A$.

The photon-counting detectors PCDM+1 through PCDN intermittently detect the X-rays that have been transmitted through the object with a predetermined detector fan beam angle $\theta_A$, and individually output a count of photons for each of predetermined energy bins. On the other hand, the detector elements in the detector 103 continuously detect the X-rays that have been transmitted through the object and output the detected signals as the detector 103 rotates.

The PCDs can be grouped as needed to be opened or closed as a group when the X-ray focal spot is arriving. According to embodiments disclosed herein, the configuration of each group can be varied in order to optimize performance and scalability. Thus, while the whole set of photon-counting detectors PCD1 through PCDN can be divided into 4 subsets as described below, it is recognized that the whole set of PCDs can alternatively be divided into N subsets (e.g., N=4, 8, or 16 for example), with the size of the subset being optimized based on cost, performance, yield, testing time scalability, reliability, etc.

Figure 5:
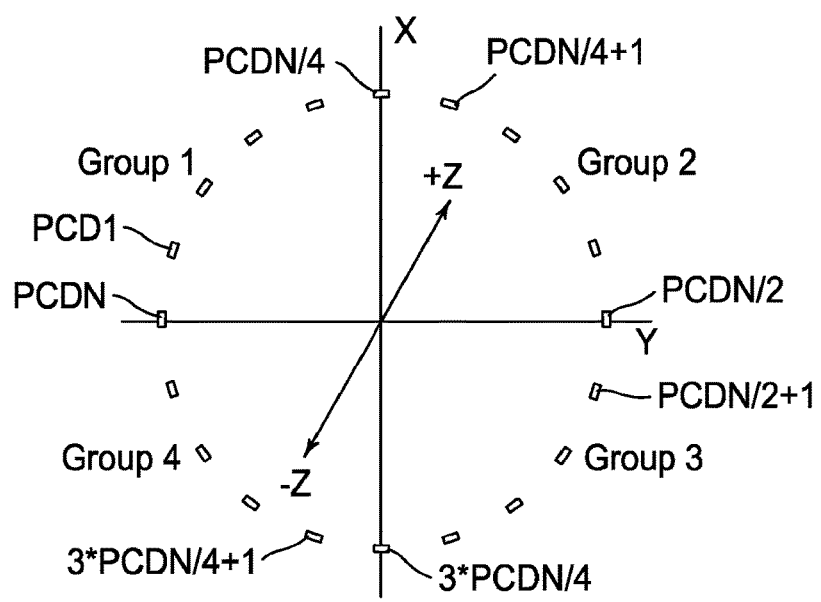
FIG. 5 shows an exemplary grouping of the photon-counting detectors.

FIG. 5 shows an exemplary of grouping of PCD detectors. The photon-counting detectors PCD1 and PCDN are divided into four groups of PCDs. The first subset (group) includes PCD1 to PCDN/4, the second subset (group) includes PCDN/4+1 through PCDN/2, the third subset (group) includes PCDN/2+1 through 3*PCDN/4, and the fourth subset (group) includes 3*PCDN/4+1 through PCDN.

Figure 6A:
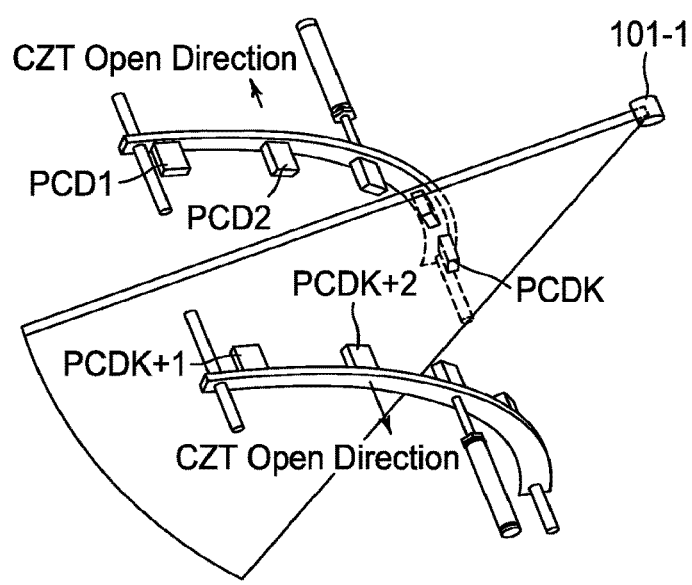
FIG. 6A shows two exemplary opened subsets of the photon-counting detectors.

FIG. 6A shows two exemplary opened subsets of the photon-counting detectors. The first subset of the PCDs (PCD1 through PCDK) is at a upper side of the trajectory plane of the X-ray source 101-1 and the second subset of the PCDs (PCDK+1 through PCDM) is at a lower side of the trajectory plane of the X-ray source 101-1 so that the emitted X-rays are no longer blocked by PCD1 through PCDK.

Figure 6B:
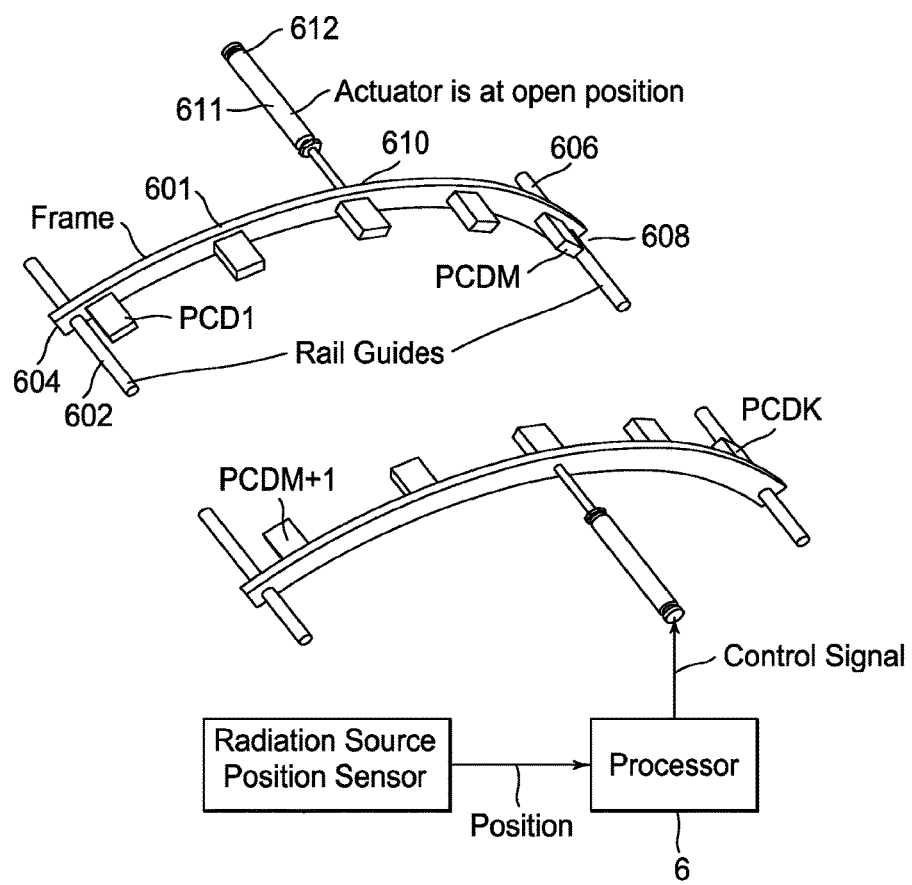
FIG. 6B shows a detail structure of the opened subsets of the photon-counting detectors.

FIG. 6B shows a detailed structure of the opened subsets of the photon-counting detectors. Based on the predetermined number of subsets N, each subset occupies a 1/Nth of a circular frame 601, an actuator 611, and two rail guides 602 and 606. The photon-counting detectors are sparsely and fixe distributed on the portion of the circular frame 601. A first rail guide 602 is located at a first end 604 of the circular frame 601, a second rail guide 606 is located at the second end 608 of the circular frame 601. A first end 610 of the actuator 611 is located in the middle of the circular frame 601. The actuator 611, which has a second end 612, is configured to move the circular frame 601 either to the upper side or to the lower side of the trajectory plane of the X-ray.

The processor 6 shown in FIG. 1 determines the location of the X-ray source 101-1 and the precise opening time of the PCDs in the X-Y plane based on the rotation position of the X-ray beam, and ensures that the PCDs that block the X-rays to the object are moved out of the X-ray beam, so that only PCDs required for collecting the radiation lie in the path of the X-ray beam. Since the processor 6 controls the position of the X-ray source 101-1 as it rotates, the processor 6 knows the position of the X-ray source 101-1 at all times. Alternatively, sensors can be used to detect position of the X-ray source 101-1. A control signal is sent to the actuator 611 from the processor 6 to move the circular frame 601 along the first rail guide 602 and the second rail guide 606. As shown in FIG. 6A, under the control of the processor 6, the actuator 611 has moved the first subset of PCDs (PCD1 through PCDK) to the upper side of the trajectory of the X-ray beam, and the second sub-set of PCDs (PCDK+ through PCDM) to the lower side of the trajectory of the X-ray beam.

The frequency of the subsets of PCDs, opening and closing is defined by:

$$\text{subset open/close frequency (Hz)} = \frac{\text{Third-generation } CT \text{ detector rotations per minute}}{60*N} \quad (1)$$

wherein the third-generation CT detector is the energy-integrating detector 103, and N is the number of the subsets of the PCDs that move together.

Figure 7:
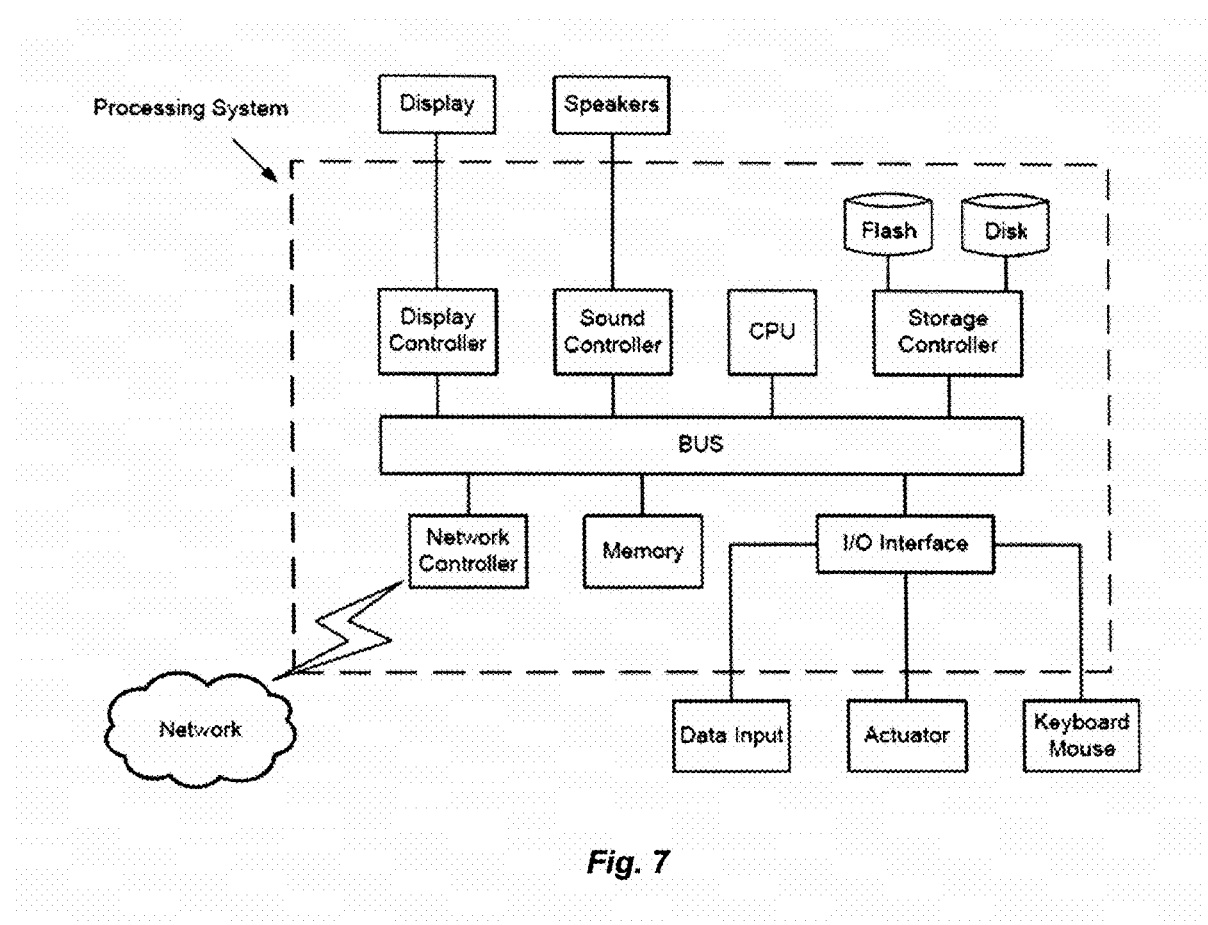
FIG. 7 shows a schematic diagram of an exemplary processing system.

In the disclosed embodiment, a pair of PCD detector subsets in the X-Y plane open in opposite directions simultaneously with precise timing control. The opening motion can be driven by an electro-mechanical system, which includes sensors, step motors, and actuators. A pure mechanical system, which includes gears, sling rings, etc., can also be used to implement the system. The electro-mechanical system includes a subsession frame including a first rail guide at a first end of the frame, a second rail guide at the second end of the frame, and the actuator to move the frame along the first and second rail guides An exemplary computer processing system is illustrated in FIG. 7, which can include the processor 6 shown in FIG. 1. The processor 6 can be a hardware device, e.g., a CPU that has been specifically configured to execute one or more computer programs that cause the CPU to perform the described function. In particular, this exemplary processing system can be implemented using one or more microprocessors or the equivalent, such as a central processing unit (CPU) and/or at least one application-specific processor ASP (not shown). A microprocessor is a circuit or circuitry that utilizes a computer readable storage medium, such as a memory circuit (e.g., ROM, EPROM, EEPROM, flash memory, static memory, DRAM, SDRAM, and their equivalents), configured to control the microprocessor to perform and/or control the processes and systems of this disclosure, and configured to execute the algorithms described herein. Other storage mediums can be controlled via a controller, such as a disk controller, which can controls a hard disk drive or optical disk drive.

The microprocessor or aspects thereof, in alternate implementations, can include or exclusively include a logic device for augmenting or fully implementing aspects of this disclosure. Such a logic device includes, but is not limited to, an application-specific integrated circuit (ASIC), a field programmable gate array (FPGA), a generic-array of logic (GAL), and their equivalents. The microprocessor can be a separate device or a single processing mechanism. Further, this disclosure can benefit from parallel processing capabilities of a multi-cored CPU and a graphics processing unit (GPU) to achieve improved computational efficiency. One or more processors in a multi-processing arrangement may also be employed to execute sequences of instructions contained in memory. Alternatively, hard-wired circuitry may be used in place of or in combination with software instructions. Thus, the exemplary implementations discussed herein are not limited to any specific combination of hardware circuitry and software.

In another aspect, results of processing in accordance with this disclosure can be displayed via a display controller to a monitor. The display controller preferably includes at least one graphic processing unit, which can be provided by a plurality of graphics processing cores, for improved computational efficiency. Additionally, an I/O (input/output) interface is provided for inputting signals and/or data from microphones, speakers, cameras, a mouse, a keyboard, a touch-based display or pad interface, etc., which can be connected to the I/O interface as a peripheral. For example, a keyboard or a pointing device for controlling parameters of the various processes or algorithms of this disclosure can be connected to the I/O interface to provide additional functionality and configuration options, or control display characteristics. Moreover, the monitor can be provided with a touch-sensitive interface for providing a command/instruction interface.

The above-noted components can be coupled to a network, such as the Internet or a local intranet, via a network interface for the transmission or reception of data, including controllable parameters. A central BUS is provided to connect the above hardware components together and provides at least one path for digital communication there between.

Further, the processing systems, in one implementation, can be connected to each other by a network or other data communication connection. One or more of the processing systems can be connected to corresponding actuators to actuate and control movement of the gantry, the X-ray source, and/or the patient bed.

Suitable software can be tangibly stored on a computer readable medium of a processing system, including the memory and storage devices. Other examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read. The software may include, but is not limited to, device drivers, operating systems, development tools, applications software, and/or a graphical user interface.

Computer code elements on the above-noted medium may be any interpretable or executable code mechanism, including but not limited to scripts, interpretable programs, dynamic link libraries (DLLs), Java classes and complete executable programs. Moreover, parts of the processing of aspects of this disclosure may be distributed for better performance, reliability and/or cost.

The data input portion of the processing system accepts input signals from a detector or an array of detectors by, e.g., respective wired connections. A plurality of ASICs or other data processing components can be provided as forming the Data Input portion, or as providing input(s) to the data input portion. The ASICs can receive signals from, respectively, discrete detector arrays or segments (discrete portions) thereof. When an output signal from a detector is an analog signal, a filter circuit can be provided, together with an analog-to-digital converter for data recording and processing uses. Filtering can also be provided by digital filtering, without a discrete filter circuit for an analog signal. Alternatively, when the detector outputs a digital signal, digital filtering and/or data processing can be performed directly from the output of the detector.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. A computed tomography (CT) imaging apparatus, comprising:
    a radiation source configured to emit X-rays while rotating in a predetermined trajectory;
    a plurality of detectors arranged in a circular ring and configured to detect the emitted X-rays; and
    processing circuitry configured to:
        cause the radiation source to scan an object, and
        cause a subset of the plurality of detectors nearest to the radiation source to move in a direction intersecting with a plane of the predetermined trajectory of the radiation source in accordance with a determined location of the radiation source.

2. The CT imaging apparatus of claim 1, wherein the processing circuitry is further configured to determine the location of the radiation source.

3. The CT imaging apparatus of claim 1, wherein the plurality of detectors include photon-counting detectors (PCDs), and the processing circuitry is further configured to cause the radiation source to rotate in the predetermined trajectory.

4. The CT imaging apparatus of claim 3, further comprising:
    a CT detector, which includes a plurality of energy-integrating detectors, configured to rotate together with the radiation source, wherein the PCDs are arranged in the circular ring with a radius smaller than a radius of the predetermined trajectory of the radiation source.

5. The CT imaging apparatus of claim 3, wherein the processing circuitry is further configured to cause the subset of the plurality of detectors to move at a frequency that is proportional to a rotation speed of the radiation source, and inversely proportional to a size of the subset.

6. The CT imaging apparatus of claim 1, further comprising an electro-mechanical system connected to the plurality of detectors, wherein the processing circuitry is further configured to cause the subset of the plurality of detectors to move by sending a control signal to the electro-mechanical system.

7. The CT imaging apparatus of claim 6, wherein the electro-mechanical system includes a sensor and an actuator.

8. The CT imaging apparatus of claim 7, wherein the electro-mechanical system includes a subsession frame including a first rail guide at a first end of the subsession frame, a second rail guide at a second end of the subsession frame, and the actuator to move the subsession frame along the first rail guide and the second rail guide.

9. The CT imaging apparatus of claim 1, wherein the subset of the plurality of detectors includes a first subset at an upper side of the plane and a second subset at a lower side of the plane, and the processing circuitry is further configured to cause the first subset and the second subset to move in opposite directions.

10. A computed tomography (CT) imaging method for a CT apparatus that includes a plurality of detectors arranged in a circular ring and configured to detect X-rays emitted from a radiation source that rotates in a predetermined trajectory, the CT imaging method comprising:
    causing the radiation source to scan an object, and
    causing a subset of the plurality of detectors nearest to the radiation source to move in a direction intersecting with a plane of the predetermined trajectory of the radiation source in accordance with a determined location of the radiation source.

11. The CT imaging method of claim 10, further comprising causing the radiation source to rotate in the predetermined trajectory.

12. The CT imaging method of claim 10, further comprising causing a subset of the plurality of detectors to move by sending a control signal to an electro-mechanical system connected to the plurality of detectors.

13. The CT imaging method of claim 10, wherein the plurality of detectors include photon-counting detectors (PCDs), the method further comprising causing a subset of the PCDs to move by sending a control signal to an electro-mechanical system that includes a subsession frame including a first rail guide at a first end of the subsession frame, a second rail guide at a second end of the subsession frame, and an actuator to move the subsession frame along the first rail guide and the second rail guide.

14. The CT imaging method of claim 10, further comprising causing the subset of the plurality of detectors to move at a frequency that is proportional to a rotation speed of the radiation source and inversely proportional to a size of the subset.

15. The CT imaging method of claim 10, further comprising causing a first subset of the plurality of detectors at an upper side of the plane and a second subset of the plurality of detectors at an lower side of the plane to move in opposite directions.

16. A non-transitory computer-readable medium storing executable instructions, which when executed by a computer processor of a CT apparatus that includes a plurality of detectors arranged in a circular ring and configured to detect X-rays emitted from a radiation source that rotates in a predetermined trajectory, cause the computer processor to execute a method comprising:
    causing the radiation source to scan an object, and
    causing a subset of the plurality of detectors nearest to the radiation source to move in a direction intersecting with a plane of the predetermined trajectory of the radiation source in accordance with a determined location of the radiation source.

* * * * *